United States Patent
Vancamberg et al.

(10) Patent No.: US 9,265,587 B2
(45) Date of Patent: Feb. 23, 2016

(54) METHOD FOR DETERMINING AN INSERTION TRAJECTORY OF A TOOL IN A DEFORMABLE TISSULAR MATRIX AND ROBOTIC SYSTEM EXECUTING THE METHOD

(75) Inventors: Laurence Vancamberg, Le Port Marly (FR); Anis Sahbani, Bagneux (FR); Serge Muller, Guyancourt (FR); Guillaume Morel, Malakoff (FR)

(73) Assignees: General Electric Company, Schenectady, NY (US); Centre National de la Recherche Scientifique, Paris (FR); Universite Pierre et Marie Curie, Paris (FR)

( * ) Notice: Subject to any disclaimer, the term of this patent is extended or adjusted under 35 U.S.C. 154(b) by 679 days.

(21) Appl. No.: 13/099,418

(22) Filed: May 3, 2011

(65) Prior Publication Data

US 2011/0270270 A1   Nov. 3, 2011

(30) Foreign Application Priority Data

May 3, 2010   (FR) ...................................... 10 01897

(51) Int. Cl.
*A61B 19/00*   (2006.01)
*A61B 10/02*   (2006.01)
*A61B 17/00*   (2006.01)

(52) U.S. Cl.
CPC ................. *A61B 19/50* (2013.01); *A61B 10/02* (2013.01); *A61B 19/5244* (2013.01); *A61B 2017/00716* (2013.01); *A61B 2019/507* (2013.01)

(58) Field of Classification Search
CPC ............. A61B 19/50; A61B 2019/501; A61B 2019/502; A61B 2019/504; A61B 2019/505; A61B 2019/507; A61B 10/02
USPC .......... 606/130, 148, 32, 34, 41, 44; 703/6, 7, 703/11; 600/7, 424–429, 461, 562, 600/564–567, 587; 604/116, 93.01, 264, 604/272
See application file for complete search history.

(56) References Cited

U.S. PATENT DOCUMENTS

| 5,219,351 | A | 6/1993 | Teubner et al. |
| 8,348,861 | B2 * | 1/2013 | Glozman et al. ............. 600/587 |

(Continued)

FOREIGN PATENT DOCUMENTS

| DE | 102007015929 A1 | 10/2008 |
| IL | WO 2007/141784 | * 12/2007 |

(Continued)

OTHER PUBLICATIONS

Alterovitz, R., Goldberg, K.: Motion Planning on Medicine: Optimization and Simulation Algorithms for Image-Guided Procedures. Springer Tracts in Advanced Robotics, vol. 50, 27-55 (2008).*

(Continued)

*Primary Examiner* — Jonathan W Miles
*Assistant Examiner* — Todd J Scherbel
(74) *Attorney, Agent, or Firm* — Global Patent Operation; Marc A. Vivenzio

(57) ABSTRACT

A method for determining an insertion trajectory of a tool for reaching a moving target object prior to its insertion into a tissular matrix. The method comprises acquiring images of the tissular matrix, constructing a three-dimensional representation of the tissular matrix, determining coordinates of the initial position of the target object and any obstacles, and determining at least one potential trajectory of the tool from the coordinates of any obstacles and the initial position of the target object. The method further comprises simulating insertion of the tool in the tissular matrix to determine displacement of the target object during insertion of the tool up to the initial position of the target object along a potential trajectory, determining a new position of the target object based on the determined displacement, and determining the insertion trajectory for the new position of the target object.

9 Claims, 5 Drawing Sheets

(56) References Cited

U.S. PATENT DOCUMENTS

| | | | |
|---|---|---|---|
| 2008/0287827 A1 | 11/2008 | Sarkar et al. | |
| 2009/0149867 A1* | 6/2009 | Glozman et al. | 606/130 |
| 2010/0076305 A1 | 3/2010 | Maier-Hein et al. | |
| 2010/0130858 A1* | 5/2010 | Arai et al. | 600/443 |
| 2011/0112549 A1* | 5/2011 | Neubach et al. | 606/130 |

FOREIGN PATENT DOCUMENTS

| | | | |
|---|---|---|---|
| JP | 2006149560 A | | 6/2006 |
| JP | WO 2007/040270 | * | 10/2006 |
| JP | 2009226087 A | | 10/2009 |
| WO | 2006089426 A1 | | 8/2006 |
| WO | 2006119426 A2 | | 11/2006 |
| WO | 2007042986 A2 | | 4/2007 |
| WO | 2007095330 A2 | | 8/2007 |
| WO | 2007095637 A1 | | 8/2007 |

OTHER PUBLICATIONS

Baegert C., et al., "Multi-criteria trajectory planning for hepatic radiofrequency ablation" Medical Image Computing and Computer-Assisted Intervention MICCIA 2007, pp. 676-684.

Alterovitz, R., et al., "Steering Flexible Needles Under Markov Motion Uncertainty", IEEE International Conference on Intelligent Robots and Systems (IROS), Aug. 2005, pp. 120-125.

Alterovitz, R., et al., "Constant-Curvature Motion Planning Under Uncertainty with Applications in Image-Guided Medical Needle Steering", Workshop on the Algorithmic Foundations of Robotics, 2006.

Duindam, V., et al., "Screw-Based Motion Planning for Bevel-Tip Flexible Needles in 3D Environments with Obstacles", IEEE International Conference on Robotics and Automation (ICRA), 2008.

Duindam, V., et al., "3D Motion Planning Algorithms for Steerable Needles Using Inverse Kinematics", 8th Workshop on the Algorithmic Foundations of Robotics, 2008.

Xu, J., et al., "Motion Planning for Steerable Needles in 3D Environments with Obstacles Using Rapidly-Exploring Random Trees and Backchaining", IEEE Int. Conf. on Automation Science and Engineering (CASE), 2008.

Dimaio, S.P., et al, "Needle Steering and Motion Planning in Soft Tissues", IEEE Trans. on Biomedical Engineering, 2004.

Hauser, K. et al., "Feedback Control for Steering Needles Through 3D Deformable Tissue Using Helical Paths", Robotics: Science and Systems V, 2009.

Dehghan, E., et al., "Needle Insertion Parameter Optimization for Brachytherapy", IEEE Trans. on Robotics, vol. 25, No. 2, Apr. 2009, pp. 303-315.

Unofficial translation of Search Report and Written Opinion from FR Application No. 1001897 dated Jan. 4, 2011.

Vancamberg, L. et al.,"Needle Path Planning for Digital Breast Tomosynthesis Biopsy", IEEE International Conference on Robotics and Automation (ICRA), 2010.

Vancamberg, L. et al., "Needle Path Planning Method for Digital Breast Tomosynthesis Biopsy Based on Probabilistic Techniques" International Workshop on Digital Mammography (IWDM) 2010.

Unofficial English Translation of Japanese Office Action issued in connection with corresponding JP Application No. 2011-094589 on Feb. 17, 2015.

* cited by examiner

METHOD FOR DETERMINING AN INSERTION TRAJECTORY OF A TOOL IN A DEFORMABLE TISSULAR MATRIX AND ROBOTIC SYSTEM EXECUTING THE METHOD

BACKGROUND OF THE INVENTION

1. Field of the Invention

The field of the invention generally relates to medical imaging and more particularly relates to methods for determining an insertion trajectory of a tool for reaching a target object, prior to its insertion into a tissular matrix, moving within the tissular matrix, from image acquisition suitable for producing a three-dimensional representation of the tissular matrix.

The field of the invention also relates to the field of robotic systems for positioning a tool for reaching a target object, prior to its insertion into a tissular matrix, within the tissular matrix, from a determination of an insertion trajectory.

2. Description of the Prior Art

Determining an insertion trajectory of a tool for reaching a target object to be inserted into a tissular matrix within the tissular matrix is important in the medical field.

Indeed, chances of success for intervention depend on this determination, since incorrect or insufficiently accurate determination can result in failure in the attempt to reach the target object, or can even cause complications potentially serious for the health of the patient due to damage to some tissue or organs as the tool is moving through the tissular matrix.

Therefore, the medical world is actively researching methods for determining an insertion trajectory.

By way of example, document "*Multi-criteria trajectory planning for hepatic radiofrequency ablation*" by Baegert et al., in "*Medical Image Computing and Computer-Assisted Intervention—MICCAI 2007*", 2007, discloses a method for determining an insertion trajectory for the insertion of a needle for hepatic radiofrequency ablation. This method takes into account a number of parameters, including some strict criteria, such as the needle not passing through a vital organ, bone or a major blood vessel; and other flexible criteria. Associated with each criterion is a function reflecting the state of the criterion as a function of a trajectory taken by the needle. A macro-function is then created by weighted addition of functions. Minimization of the macro-function gives the insertion trajectory.

However, this method does not take into account deformation of the tissular matrix into which the tool is inserted. Yet, deformation of the tissular matrix causes displacement of the target object. Therefore, even though the trajectory has been optimized by this method, it is still possible to miss the target object or touch other tissue.

A method for brachytherapy is known from "*Needle Insertion Parameter Optimization for Brachytherapy*", by Dehghan et al., in "*IEEE Transactions on Robotics*", Col. 25, No. 2, April 2009. In this method, the aim is to reach a plurality of target objects at the same time. In order to find the insertion trajectory, simulation of the deformation of the prostate, during insertion of the needle along a line passing very close to the target objects, is carried out to detect displacement of the target objects. A new trajectory passing very close to the new positions is determined from the new positions of the target objects. Simulation of the deformation of the prostate, during insertion of the needle along the new trajectory, is carried out, here again, to detect displacement of the target objects.

The steps for determining a new trajectory and of simulation are reiterated until the distance between the needle and the target objects which are displaced is under a threshold, the latter trajectory being the insertion trajectory.

However, this method cannot be applied to determining an insertion trajectory to reach a single target object. In fact, application of the method requires being able to determine the trajectory passing very close to the target objects. Yet, there is no single solution when there is only a single target object. Rather, there are an endless number of solutions.

SUMMARY OF THE INVENTION

A method for determining an insertion trajectory of a tool for reaching a moving target object prior to its insertion into a tissular matrix is provided. The tissular matrix comprises obstacles, and the target object has an initial position. The method comprises acquiring images of the tissular matrix. The method further comprises constructing a three-dimensional representation of the tissular matrix from the images. The method further comprises determining coordinates of the initial position of the target object and coordinates of the obstacles. The method further comprises determining at least one potential trajectory of the tool from the coordinates of the obstacles of the tissular matrix and of the coordinates of the initial position of the target object, wherein in the potential trajectory, the tool encounters no obstacles up to the initial position of the target object during insertion. The method further comprises simulating insertion of the tool in the tissular matrix to determine displacement of the target object within the tissular matrix during insertion of the tool up to the initial position of the target object along the potential trajectory. The method further comprises determining a new position of the target object based on the determined displacement, and determining the insertion trajectory for the new position of the target object.

An advantage of this method is that it enables accurately reaching a target object moving within a tissular matrix without touching the obstacles. This method helps minimize the risks of failure and medical complication.

Another advantage is that the patient does not need to be repositioned, should his position correspond to a position outside an intervention window of the prior art. Indeed, the present method enables reaching the target object along multiple trajectories having varied orientations.

A robotic system for positioning a tool to be inserted into a tissular matrix to reach a moving target object within the tissular matrix, wherein the tissular matrix comprises obstacles, is also provided. The system comprises an imaging module configured to acquire a three-dimensional image of the tissular matrix and to determine coordinates of an initial position of the target object and coordinates of the obstacles. The system further comprises a tool support. The system further comprises a determination module configured to: determine an insertion trajectory of the tool from the coordinates of the initial position of the target object and the obstacles; determine at least one potential trajectory of the tool from the coordinates of the obstacles of the tissular matrix and of the coordinates of the initial position of the target object, wherein in the potential trajectory, the tool encounters no obstacles up to the initial position of the target object during insertion; simulate insertion of the tool in the tissular matrix to determine displacement of the target object within the tissular matrix during insertion of the tool up to the initial position of the target object along the potential trajectory; determine a new position of the target object based on the determined displacement; and determine the insertion trajectory for the new position of the target object. The system further comprises a positioning module configured to position the tool based on the determined insertion trajectory by displacing the tool support so that the tool is positioned according to the insertion trajectory.

Finally, a computer program is proposed comprising machine instructions for executing the method presented hereinabove.

BRIEF DESCRIPTION OF THE DRAWINGS

Other aims, features and advantages will become apparent from the following description in reference to the illustrating and non-limiting drawings, among which.

DETAILED DESCRIPTION OF THE INVENTION

Throughout the description, the term trajectory means a set of parameters for defining the path of a tool to be inserted into a tissular matrix. These parameters can vary and depend on the system of coordinates used.

By way of example, a trajectory can be defined, in a previously selected reference frame, by the coordinates of an insertion point of the tool in the tissular matrix and the coordinates of a point of arrival of the tool in the tissular matrix after its insertion. The trajectory may further be defined by the coordinates of an insertion point of the tool, two angles with respect to the axes of the previously selected reference frame, and an insertion length.

In these two examples, these parameters are sufficient for a rectilinear trajectory, whereas for a curved trajectory, a radius of curvature can complete these parameters.

The determination of a trajectory is therefore understood by determination of these parameters.

Figure 8:
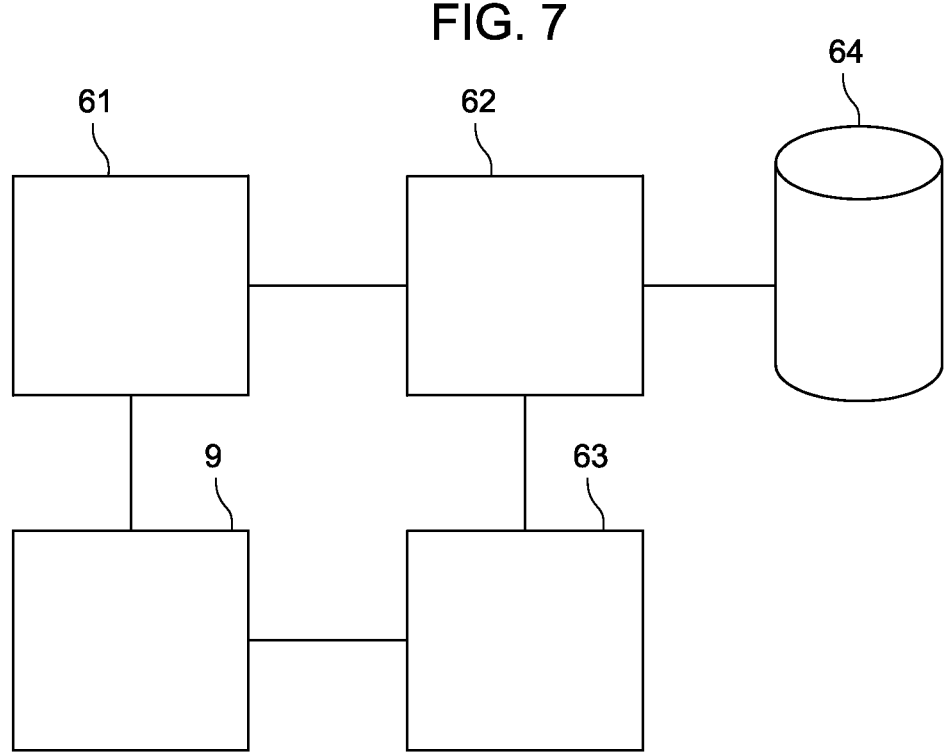
FIG. 8 is a schematic illustration of a medical imaging module of the robotic system.

FIG. 8 schematically illustrates a medical imaging module 6 for acquiring images that enable three-dimensional construction of a tissular matrix 9.

The medical imaging module 6 can be mammograph equipment for detection and characterization of lesions (target objects) in the case of screening, diagnosis and treatment of breast (tissular matrix) cancer.

The medical imaging module comprises for example a two-dimensional acquisition unit 61 for acquiring sectional images of the tissular matrix 9, an image-processing unit 62 for reconstruction of the three-dimensional image from the sectional images of the tissular matrix 9, and a display unit 63.

The acquisition unit 61 acquires a plurality of 2D projections of a region of interest, for example, of a tissular matrix 9, of a patient. The acquisition unit 61 comprises for example a detector located opposite an X-ray source. The detector may be a digital camera for example. The acquisition unit 61 may be, for example, an X-ray acquisition unit, the latter comprising any known means for X-ray emission into tissular matrix 9 and acquisition of resulting images.

The display unit 63 can be integrated in the image-acquisition unit 61 or the image-processing unit 62, or be separated from the acquisition unit 61 and the processing unit 62.

The display unit 63 is for example a computer screen, a monitor, a flat screen, a plasma screen or any type of commercially known display device.

The display unit 63 allows a practitioner to control the reconstruction and/or display of two-dimensional images acquired.

The processing unit 62 is adapted for executing treatment methods, for example, reconstruction of a three-dimensional image from two-dimensional images. The processing unit 62 can be integrated in the image-acquisition unit 61 or be separated from the image-acquisition unit 61.

The processing unit 62 is for example a computer(s), a processor(s), a microcontroller(s), a micro-computer(s), a programmable automaton(s), a specific application integrated circuit(s), other programmable circuits, or other devices including a computer such as a workstation.

The processing unit 62 is coupled to memory units 64 which can be integrated in or separated from the processing unit 62. These memory units 64 can be formed by a hard drive or SSD, or any other removable and rewritable stockage means (USB drives, memory cards, etc.).

These memory units 64 can serve to store a three-dimensional image of the zone of the organ viewed as an acquired or processed two-dimensional image. It can be ROM/RAM memory of the processing unit, a USB drive, a memory card, and central server memory.

The processing unit 62 can comprise a reader (not shown) for example a disc reader or a CD-ROM reader, for reading the instructions of the processing method of instruction medium (not shown), such as a disc or a CD-ROM or more generally by any removable memory medium or even via a network connection.

As a variant, the processing unit 62 can comprise a wired or wireless network connection device (not shown). As a variant, the processing unit 62 executes the instructions of the processing method stored in microsoftware.

Figure 1:
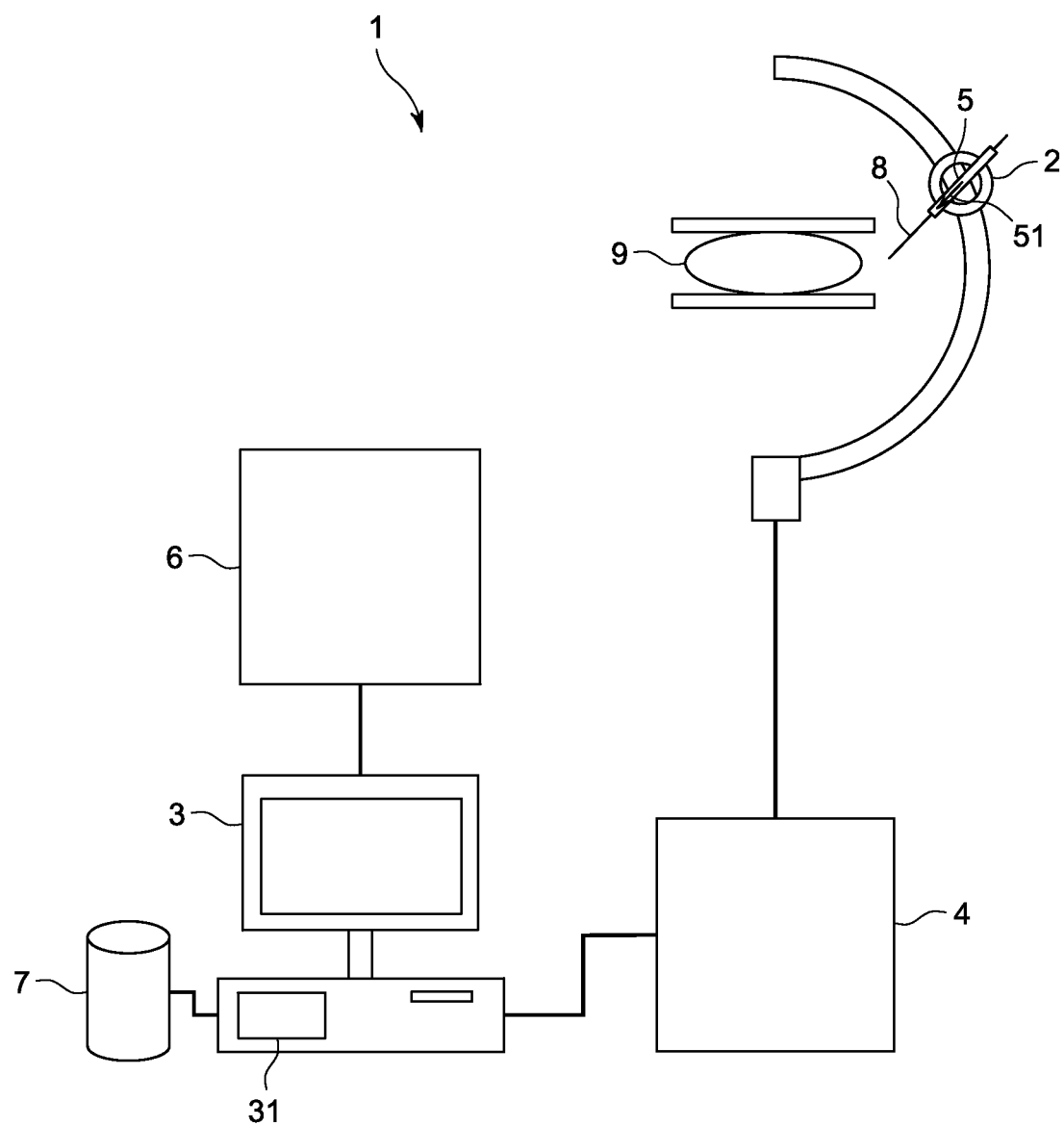
FIG. 1 is an illustration of an example of a robotic system executing a method for determining an insertion trajectory.

With reference to FIG. 1, a robotic system 1 for positioning a tool 8 to be inserted into a tissular matrix 9 is described hereinbelow.

The robotic system 1 enables positioning of the tool 8 according to various orientations so that it can reach a moving target object 9c, for example a tumor, within the tissular matrix 9 while avoiding obstacles 9o located in the tissular matrix 9 and optionally in the environment of the tissular matrix 9. The obstacles may be, for example, blood vessels.

Various orientations of the tool 8 mean that the system 1 can position the tool 8 so that it is inserted into the tissular matrix 9 other than by lateral and vertical approach. However, these two types of approach are also possible with the system 1.

To this aim, the system 1 comprises a medical imaging module 6 for acquiring images of the tissular matrix 9, for creating a three-dimensional representation of the tissular matrix 9 from the acquired images, and determining coordinates of an initial position $P_{in}$ of the target object 9c and of the obstacles 9o. This medical imaging device 6 can be for example a device for digital breast tomosynthesis.

The system 1 also comprises a module 3 for determining an insertion trajectory $T_{ins}$ of the tool 8 from the coordinates of the initial position $P_{in}$ of the target object 9c. This determination module 3 executes a method for determining the insertion trajectory $T_{ins}$, which will be described hereinbelow, via a simulation unit 31 for simulating displacements of the target object 9c during insertion of the tool 8 into the tissular matrix 9.

The determination module 3 can be the processing unit 62 of the medical imaging module 6.

The determination module 3 is for example a computer(s), a processor(s), a microcontroller(s), a micro-computer(s), a programmable automaton(s), a specific integrated application circuit(s), other programmable circuits, or other devices including a computer such as a workstation.

The determination module 3 is coupled to the memory modules 7 which can be integrated in or separate from the determination module 3. These memory modules 7 can be formed by a hard drive or SSD, or any other removable and rewritable stockage means (USB drives, memory cards, etc.).

These memory modules 7 can serve to store the coordinates of the initial position $P_{in}$ of the target objects 9c and of the obstacles 9o, the parameters defining the trajectories as well as any other coordinate or parameter necessary for executing the method.

The system 1 also comprises a support 2 of the tool 8 for holding the tool 8 during its positioning.

The system 1 also comprises a module 4 for positioning the tool 8 for displacing the support 2 from the insertion trajectory $T_{ins}$ so that the tool 8 can be inserted along the insertion trajectory $T_{ins}$, making work easier for the practitioner.

The system 1 can also comprise a guide module 5 of the tool 8 along the insertion trajectory $T_{ins}$. This guide module 5 can comprise an inserter 51 for inserting the tool 8 into the tissular matrix 9, enabling automation of the insertion operation of the tool 8 during operation of an insertion method comprising the steps of the method described hereinbelow and a step of insertion of the tool 8 into the tissular matrix 9.

With reference to FIGS. 2 to 4, 5a to 5c, 6a, 6b and 7 exemplary embodiments of the method for determining an insertion trajectory $T_{ins}$ of a tool 8 to be inserted into a tissular matrix 9 are described hereinbelow. This method enables the tool 8 to reach a target object 9c moving within the tissular matrix 9.

In the method, the point of the tool 8 to be considered corresponds to the point having required local action. To make the present description more legible, the term tool 8 is used in place of the point of the tool 8 having required local action. By way of example, in case reaching the target object with a needle and touching the target object with the point of the needle are aimed at, the point of the tool 8 to be considered is the tip.

In case there is no particular point of the tool 8 having a required local action, but a zone, the barycenter of the zone is to be considered. By way of example for a biopsy needle, the point of the tool 8 to be considered is the opening on the tube of the needle, near the tip, via which the biopsy is conducted. More precisely, the barycenter of this opening will be considered.

The method can be used to prepare various operations. By way of example, the method can help determine the insertion of a biopsy needle in the case of a by digital breast tomosynthesis biopsy; or of a radiofrequency probe in the case of radiofrequency ablation.

In general, the method is used to prepare any operation in which there is an endless number of insertion points of the tool 8 for reaching a single target object 9c. In case there are several target objects 9c, these are separately processed.

The target object 9c is defined as a volume of the tissular matrix 9 in which a localized action is desired. By way of example, in the case of digital breast tomosynthesis biopsy, the target object 9c is a whole or a part of tissue suspected of being cancerous tissue. In the case of radiofrequency ablation, the target object 9c is the tissue or the organ to be wholly or partially removed.

The target object 9c has an initial position $P_{in}$ within the tissular matrix 9.

The method also allows the tool 8 to avoid obstacles 9o contained within the tissular matrix 9. There are optionally also obstacles to be avoided in the environment of the tissular matrix 9. The term avoiding obstacles means that the tool 8 passes at a certain distance from the obstacles 9o. Taking into account the obstacles during determination of the insertion trajectory $T_{ins}$ improves the comfort of the patient, for example by decreasing pain, and also improves the safety of the procedure.

In order to identify obstacles, a three-dimensional representation of the tissular matrix 9, and optionally of its environment, is created in a first step a, from acquisition of images of the tissular matrix 9, and optionally of its environment. The acquisition of images and the creation of a three-dimensional representation of the tissular matrix 9 can be done using any suitable medical imaging method by using the corresponding medical imaging module 6, for example by using digital breast tomosynthesis and VTK software (Visualization Toolkit) for by digital breast tomosynthesis biopsy, for obtaining a three-dimensional representation of a breast with tetrahedral meshing.

During this step a, the imaging system determines the three-dimensional coordinates of the initial position $P_{in}$ of the target object 9c, of the obstacles 9o, a surface corresponding to the set of possible insertion points of the tool 8, and the parameters of a deformation model of the tissular matrix 9 used in a later step.

The obstacles 9o can be blood vessels which are not to be touched, bone, some other organ, etc.

In order to determine the insertion trajectory $T_{ins}$, the method comprises a step b for determining at least one potential trajectory $T_p$ of the tool 8. This determination takes into account the obstacles 9o of the tissular matrix 9 so that the tool 8 encounters no obstacle 9o during its insertion up to the initial position $P_{in}$ of the target object 9c.

A potential trajectory $T_p$ is understood as a trajectory from an insertion point of the tool 8 up to the target object 9c. The form of this potential trajectory $T_p$ differs according to the form of the tool 8. By way of example, for a needle with a symmetrical tip, the trajectory is rectilinear, whereas for a needle with a bevelled tip the trajectory follows the tip of the bevel according to a curve whereof the radius of curvature depends on the angle of the bevel, the flexibility of the needle and the mechanical properties of the tissular matrix 9 into which the needle is inserted.

However, if the tool is inserted along this potential trajectory $T_p$, it is uncertain whether the tool will reach the target object 9c. Indeed, the tissular matrix 9 is soft and deforms under action of forces exerted by the tool 8 during its insertion. Therefore the target object 9c moves.

In order to increase the chances of reaching the target object 9c with the tool 8, the method also comprises a step c for determining the displacement of the target object 9c within the tissular matrix 9 during insertion of the tool 8 along the potential trajectory $T_p$ up to the initial position $P_{in}$ of the target object 9c so that the tool 8 reaches the initial position $P_{in}$. As a result of step c, a new position $P_{no}$; $P^i_{no}$ of the target object 9c is obtained, indicative of how the target object 9c moves during insertion of the tool.

Determining the new position $P_{no}$ is done by simulating the deformation of the tissular matrix 9 on the three-dimensional representation of the tissular matrix 9 previously made. Simulation uses the deformation model the parameters of which have been determined during step a; the model can be for example a finite element method using a stick-slip model of the frictions between the tissular matrix 9 and the tool 8.

Therefore, deformation of the tissular matrix 9 is taken into account here, as compared to step b.

Finally, the method comprises a step d for determining the insertion trajectory $T_{ins}$ from the new position $P_{no}$ of the target object 9c.

In a variant, the potential trajectory $T_p$ of the tool 8 can be determined by identifying a least cost trajectory $T_{min}$. Criteria identifying this least cost trajectory $T_{min}$ depend on various parameters, for example the preferred angle of insertion, the preferred insertion side which can be different according to whether people are left-handed or right-handed, etc.

A simple criterion would be the length of the trajectory between the point of insertion of the tool and the target object 9c. The least cost trajectory $T_{min}$ would then be the shortest trajectory.

Throughout the method, the object 8 is not inserted into the tissular matrix 9. The method is only a simulation of the insertion of the object 8.

Figure 2:
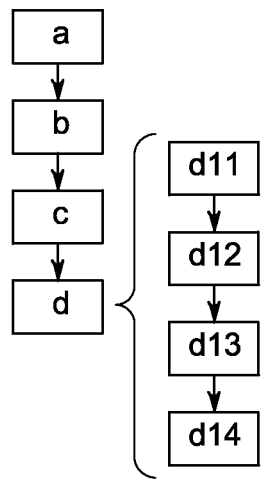
FIG. 2 is a diagram showing the steps of an exemplary embodiment of a method for determining an insertion trajectory.
Figure 6A:
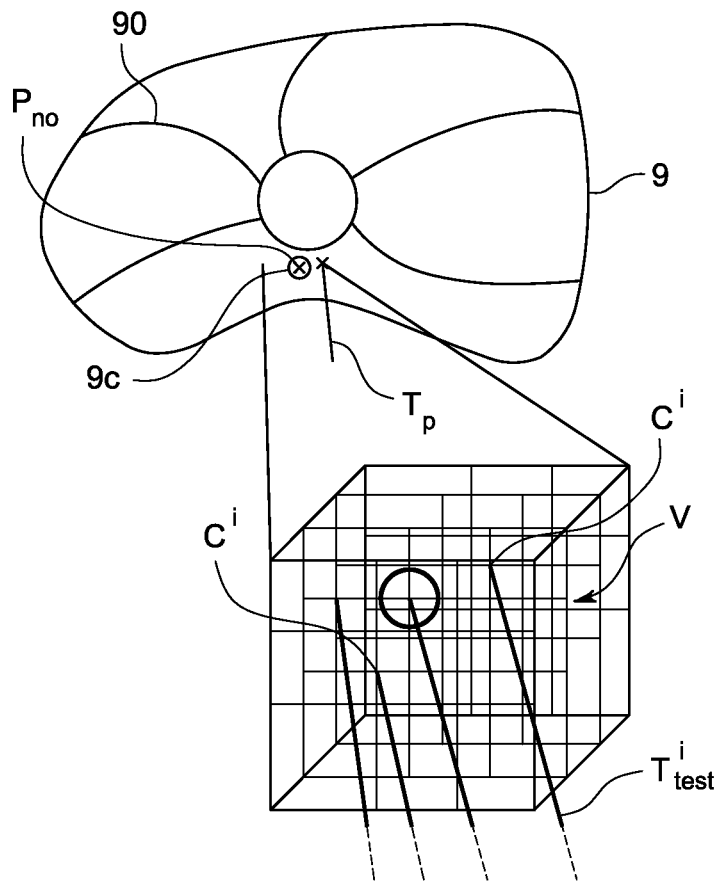
FIGS. 6a and 6b illustrate specific steps of the exemplary embodiment of FIG. 2.
Figure 6B:
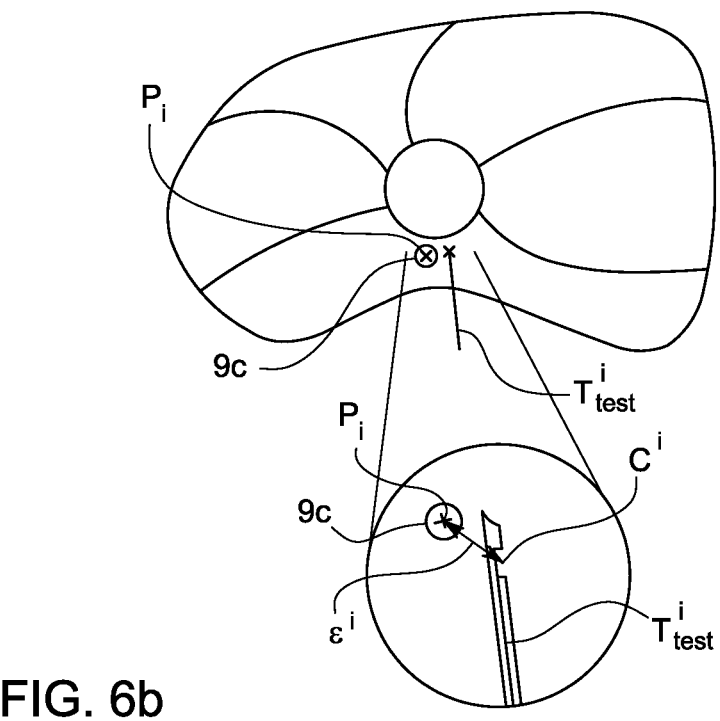

With reference to FIGS. 2, 6a and 6b, an exemplary embodiment of the method is described hereinbelow in greater detail.

In this embodiment, step d of the method comprises a sub-step d11 for generating a set of target points $\{C^i\}$ to be tested. These target points $C^i$ are selected from around the new position $P_{no}$ of the target object 9c.

By way of example, a volume V is defined around the new position $P_{no}$ of the target object 9c. Inside this volume V, a regular mesh is defined, the nodes of which form the target points $C^i$ (see FIG. 6a).

A trajectory to be tested $T^i_{test}$ is defined from each target point $C_1$. The trajectory to be tested $T^i_{test}$ is selected so as to be substantially colinear to the potential trajectory $T_p$ (see FIG. 6a) and so as not to pass through an obstacle 9o. The set of trajectories to be tested $T^i_{test}$ forms a finite family of trajectories to be tested $\{T^i_{test}\}$.

Therefore, instead of testing an unknown number of trajectories, the practitioner knows the number of trajectories to be tested, enabling knowing in advance the calculation time necessary for determining the insertion trajectory $T_{ins}$, which can be long, especially when a solution by iteration does not converge. Also, the mesh size is defined so that a mesh has the size of the transverse section of the tool 8, for example, in the case of a needle, its diameter. Therefore, there is a good chance of reaching the target object 9c.

For each of the trajectories $T^i_{test}$ of the family of trajectories, step d further comprises a sub-step d12 for determining the displacement of the target object 9c during insertion of the tool 8 along the trajectory to be tested $T^i_{test}$ up to the corresponding target point $C^i$ so that the tool 8 reaches the target point $C^i$, as in step c, that is, by simulating the deformation of the tissular matrix 9. This determination produces the position $P^i$ of the target object 9c after insertion of the tool 8 along the trajectory to be tested $T^i_{test}$.

As illustrated in FIG. 6b, for each of the trajectories $T^i_{test}$ of the family of trajectories, step d comprises another sub-step d13 for calculating an error $\epsilon^i$. The error $\epsilon^i$ is defined as the distance between the target point $C^i$ of the corresponding trajectory to be tested $T^i_{test}$ and the position $P^i$ of the target object 9c after insertion of the tool 8.

The errors $\epsilon^i$ obtained are then compared in a sub-step d14. The insertion trajectory $T_{ins}$ is selected, among the trajectories to be tested $T^i_{test}$ and the potential trajectory $T_p$, as being the trajectory having the lowest error $\epsilon^i$.

Figure 3:
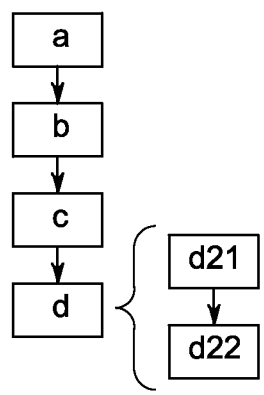
FIG. 3 is a diagram showing the steps of an exemplary embodiment of a method for determining an insertion trajectory.
Figure 7:
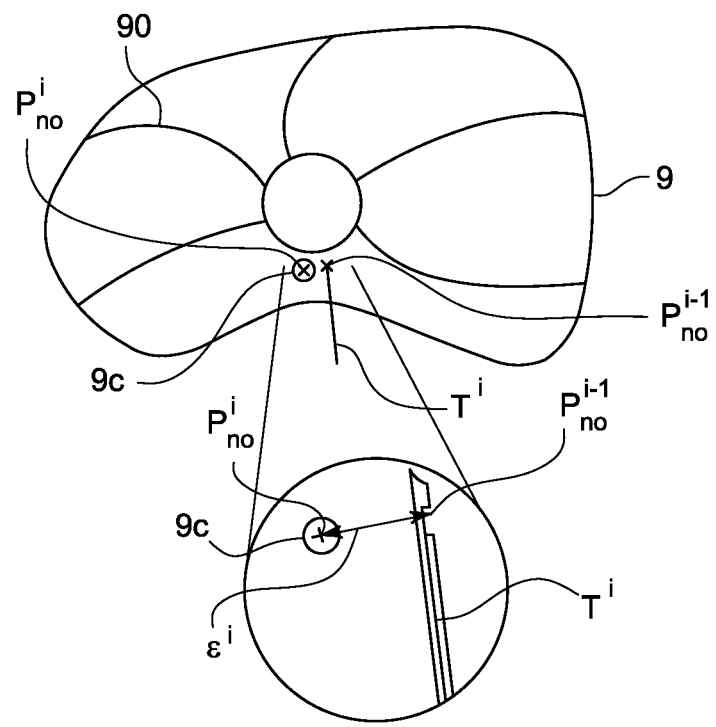
FIG. 7 illustrates one of the specific steps of the exemplary embodiments of FIGS. 3 and 4.

With reference to FIGS. 3 and 7, an alternate exemplary embodiment of the method is described hereinbelow.

In this alternate exemplary embodiment, step d is carried out by iteration. During the $i^{th}$ iteration $I_i$, step d comprises a sub-step d21 for determining the displacement of the target object 9c during insertion of the tool 8 along an $i^{th}$ trajectory $T^i$ for obtaining an $i^{th}$ position $P^i_{no}$ of the target object 9c in the same way as in step c, that is, by simulating the deformation of the tissular matrix 9. The $i^{th}$ trajectory $T^i$ is selected so as to be substantially colinear to the $i-1^{th}$ trajectory $T^{i-1}$ and arrives at a $i-1^{th}$ position $P^{i-1}_{no}$ of the target object 9c (see FIG. 7). The $i-1^{th}$ trajectory $T^{i-1}$ and the $i-1^{th}$ position $P^{i-1}_{no}$ are determined during the preceding $i-1^{th}$ iteration $I_{i-1}$. For the first iteration $I_1$, the position $P^0_{no}$ is taken as the initial position $P_{in}$ and the $0^{th}$ trajectory $T^0$ as the potential trajectory $T_p$, and corresponds to steps b and c.

Also, during the $i^{th}$ iteration, an $i^{th}$ error $\epsilon^i$ is calculated during a sub-step d22. The $i^{th}$ error $\epsilon^i$ is the distance between the $i-1^{th}$ position $P^{i-1}_{no}$ and the $i^{th}$ position $P^i_{no}$ of the target object 9c after insertion of the tool 8 along the $i^{th}$ trajectory $T^i$ up to the $i-1^{th}$ position $P^{i-1}_{no}$.

Sub-steps d21 and d22 are reiterated a finite number of times N. The insertion trajectory $T_{ins}$ is selected as the trajectory having the lowest error.

Thus, apart from the possibility of knowing the necessary calculation time, this example explores trajectories which would not have been explored if a finite number of points is previously defined in a volume enclosing the new position $T^0_{no}$ of the target object 9c, while avoiding long calculation times due to non-convergence of the method.

Figure 4:
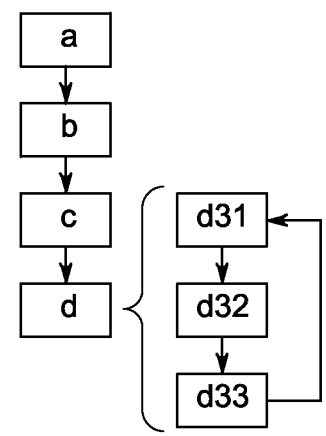
FIG. 4 is a diagram showing the steps of an exemplary embodiment of a method for determining an insertion trajectory.
Figure 5A:
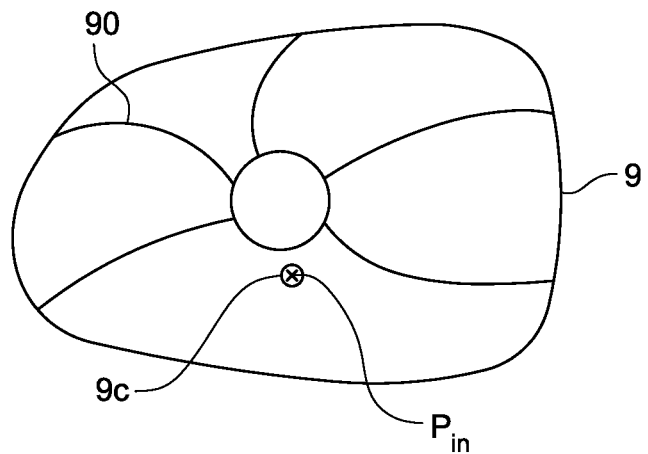
FIGS. 5a to 5c illustrate steps common to the exemplary embodiments of FIGS. 2 to 4.
Figure 5B:
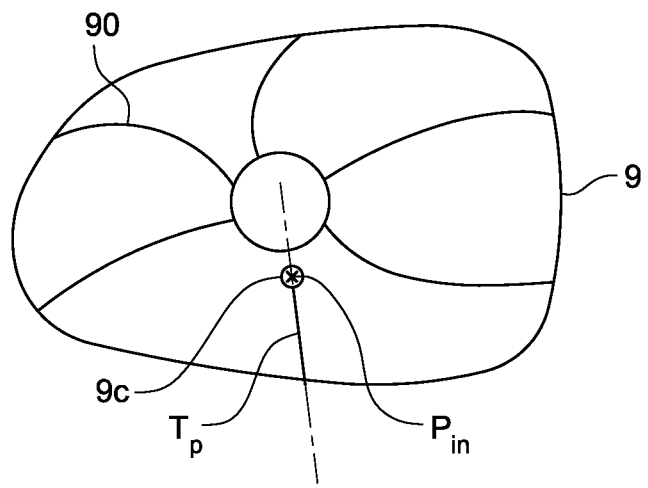
Figure 5C:
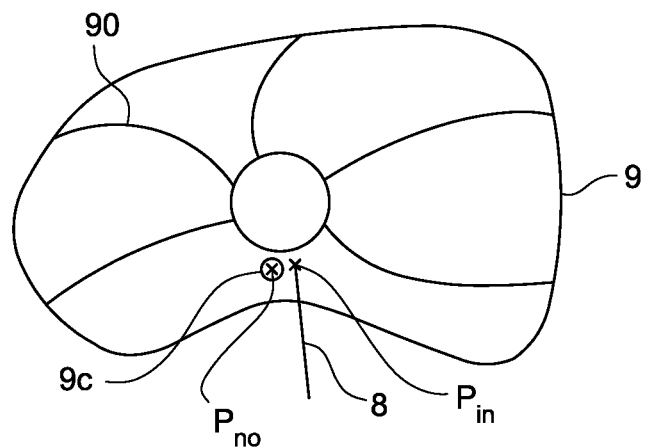

With reference to FIGS. 4 and 7, an alternate exemplary embodiment of the method is described hereinbelow. The method comprises sub-steps d31 and d32 which are the same as sub-steps d21 and d22 of the second example. The difference lies in the way the insertion trajectory $T_{ins}$ is selected. In this alternate embodiment, step d comprises, for the $i^{th}$ iteration $I_i$, a sub-step d33 of comparing the $i^{th}$ error $\epsilon^i$ to a threshold S.

If the $i^{th}$ error $\epsilon^i$ is greater than the threshold S, steps d31 and d32 are reiterated. If the $i^{th}$ error $\epsilon^i$ is less than the threshold S, the insertion trajectory $T_{ins}$ is selected as the $i^{th}$ trajectory $T^i$.

The threshold S is selected as a function of the size of the tool 8. By way of example, the threshold S is equal to a dimension characteristic of the transverse section of the tool 8, and in the case of a needle, its diameter.

The method can be executed by a computer program comprising machine instructions for this purpose.

The invention claimed is:

1. A method for determining an insertion trajectory of a tool for reaching a moving target object prior to its insertion into a tissular matrix, wherein the tissular matrix comprises obstacles, and wherein the target object has an initial position, the method comprising:
   acquiring images of the tissular matrix;
   constructing a three-dimensional representation of the tissular matrix from the images;
   determining coordinates of the initial position of the target object and coordinates of the obstacles;
   determining at least one potential trajectory of the tool from the coordinates of the obstacles of the tissular matrix and of the coordinates of the initial position of the target object, wherein in the potential trajectory, the tool encounters no obstacles up to the initial position of the target object during insertion;

simulating insertion of the tool in the three-dimensional representation of the tissular matrix to determine displacement of the target object within the tissular matrix during insertion of the tool up to the initial position of the target object along the determined potential trajectory;

determining a new position of the target object based on the determined displacement; and determining the insertion trajectory for the new position of the target object.

2. The method of claim 1, wherein the potential trajectory of the tool is determined by identifying a least cost trajectory among a set of trajectories along which the tool encounters no obstacle during insertion of the tool up to the initial position of the target object.

3. The method of claim 2, wherein the least cost trajectory is the shortest trajectory up to the initial position of the target object.

4. The method of claim 1, further comprising:

generating a set of target points to be tested around the new position of the target object; and determining a finite family of trajectories to be tested from the generated set of target points to be tested, wherein the trajectories to be tested are substantially colinear to the potential trajectory and wherein the trajectories to be tested arrive at one of the target points.

5. The method of claim 4, wherein, for each of the trajectories of the family of trajectories, the method further comprises:

determining the displacement of the target object during insertion of the tool along the trajectory to be tested to obtain the position of the target object after insertion of the tool along the trajectory to be tested;

calculating an error, wherein the error is the distance between the target point of the corresponding trajectory to be tested and the position of the target object after insertion of the tool along the trajectory to be tested;

comparing the errors among the trajectories to be tested and the potential trajectory; and selecting the insertion trajectory of the tool, wherein the insertion trajectory is the trajectory of the family of trajectories having the lowest error.

6. The method of claim 1, wherein determining the insertion trajectory for the new position of the target object is carried out by iteration, wherein for the $i^{th}$ iteration the method further comprises:

determining the displacement of the target object during insertion of the tool along an $i^{th}$ trajectory to obtain an $i^{th}$ position of the target object, wherein the $i^{th}$ trajectory is substantially colinear to an $i-1^{th}$ trajectory and wherein the $i^{th}$ trajectory arrives at the $i-1^{th}$ position of the target object;

calculating an $i^{th}$ error, wherein the $i^{th}$ error is the distance between the $i-1^{th}$ position of the target object and the $i^{th}$ position of the target object after insertion of the tool along the $i^{th}$ trajectory up to the $i-1^{th}$ position of the target object.

7. The method of claim 6, wherein determining the displacement of the target object during insertion of the tool along an $i^{th}$ trajectory and calculating an $i^{th}$ error are reiterated a finite number of times, and wherein the trajectory having the lowest error is selected to be the insertion trajectory.

8. The method of claim 6, wherein determining the insertion trajectory for the new position of the target object further comprises:

comparing the $i^{th}$ error to a threshold, wherein if the $i^{th}$ error is greater than the threshold, determining the displacement of the target object during insertion of the tool along an $i^{th}$ trajectory and calculating an $i^{th}$ error are reiterated, and if the $i^{th}$ error is less than the threshold, the $i^{th}$ trajectory is selected to be the insertion trajectory.

9. A robotic system for positioning a tool to be inserted into a tissular matrix to reach a moving target object within the tissular matrix, wherein the tissular matrix comprises obstacles, the system comprising:

an imaging module configured to acquire a three-dimensional image of the tissular matrix and to determine coordinates of an initial position of the target object and coordinates of the obstacles;

a tool support;

a determination module configured to:

determine an insertion trajectory of the tool from the coordinates of the initial position of the target object and the obstacles;

determine at least one potential trajectory of the tool from the coordinates of the obstacles of the tissular matrix and of the coordinates of the initial position of the target object, wherein in the potential trajectory, the tool encounters no obstacles up to the initial position of the target object during insertion;

simulate insertion of the tool in the three-dimensional representation of the tissular matrix to determine displacement of the target object within the tissular matrix during insertion of the tool up to the initial position of the target object along the determined potential trajectory;

determine a new position of the target object based on the determined displacement; and determine the insertion trajectory for the new position of the target object; and a positioning module configured to position the tool based on the determined insertion trajectory by displacing the tool support so that the tool is positioned according to the insertion trajectory.

* * * * *